United States Patent

Esteve-Subirana

[11] 4,038,390
[45] July 26, 1977

[54] SALTS OF P-DIHYDROXYBENZENE DISULFONIC ACIDS FOR COMBATTING HEMORRHAGES AND FRAGILITY OF THE CAPILLARIES

[75] Inventor: Antonio Esteve-Subirana, Barcelona, Spain

[73] Assignee: Laboratorios del Dr. Esteve, S.A., Barcelona, Spain

[21] Appl. No.: 601,834

[22] Filed: Aug. 4, 1975

Related U.S. Application Data

[60] Division of Ser. No. 427,679, Dec. 26, 1973, Pat. No. 3,947,448, which is a continuation-in-part of Ser. No. 359,771, May 14, 1973, abandoned.

[30] Foreign Application Priority Data

May 17, 1972 Switzerland .................. 7326/72
Jan. 26, 1973 Switzerland .................. 1154/73

[51] Int. Cl.$^2$ .................. A61K 31/495; A61K 31/40; A61K 31/185; A61K 31/205
[52] U.S. Cl. .................. 424/250; 424/274; 424/315; 424/316
[58] Field of Search ............. 424/303, 316, 250, 315, 424/274

[56] References Cited

U.S. PATENT DOCUMENTS

| | | |
|---|---|---|
| 3,354,201 | 11/1967 | Esteve-Subirana ............. 260/501.21 |
| 3,509,207 | 4/1970 | Esteve-Subirana ............. 260/512 R |
| 3,547,988 | 12/1970 | Bean ................................. 260/512 R |
| 3,629,327 | 12/1971 | Esteve-Subirana ............. 260/512 |

*Primary Examiner*—Frederick E. Waddell
*Attorney, Agent, or Firm*—Hume, Clement, Brinks, Willian & Olds, Ltd.

[57] ABSTRACT

Salts of p-dihydroxy benzene disulfonic acids having the general formula:

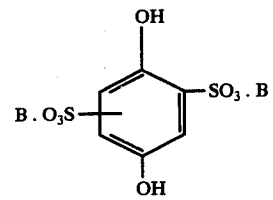

wherein B is an alkali metal or an equivalent of an alkaline-earth metal, or BH is the cation of ammonia or a nitrogen containing basic organic compound, are useful for reducing the average bleeding time and for combating capillary fragility.

23 Claims, No Drawings

SALTS OF P-DIHYDROXYBENZENE DISULFONIC ACIDS FOR COMBATTING HEMORRHAGES AND FRAGILITY OF THE CAPILLARIES

This is a divisional of co-pending application, Ser. No. 427,679, filed Dec. 26, 1973, now U.S. Pat. No. 3,947,448, which is a continuation-in-part of Ser. No. 359,771, filed May 14, 1973, now abandoned.

This invention concerns novel salts of p-dihydroxy benzene disulfonic acid, and a process for preparing said salts.

The compounds of the invention have the general formula:

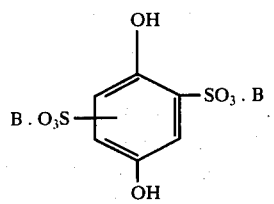

wherein B indicates an alkali metal, particularly lithium, of an equivalent of an alkaline-earth metal, particularly calcium, or BH is the cation of a nitrogen-containing basic compound such as ammonia, alkyl, alkanol, aryl, alkylaryl amines, cyclo-amines, and generally all the nitrogen-containing basic compounds capable of forming salts with p-dihydroxy benzene disulfonic acid.

The compounds of the invention are useful as hemostatic agents, and for protecting capillary fragility.

The activity for the hemostatic action is determined in vivo, by ROSKAM's method, as modified by LAPORTE, on the rabbit's ear, and the protection action on the capillaries by the method of BEACH and STEINETZ. The therapeutical index (ratio between $LD_{50}$ and $TE_{50}$) is very favorable, in view of the high activity and low toxicity.

The process of preparation according to this invention is characterized in that a p-dihydroxy benzene disulfonic acid is neutralized with a base of the cation of formula B, or in that an exchange reaction is effected between a metal salt of p-dihydroxy benzene disulfonic acid, and a salt of the B cation with another acid. Preferably, the starting p-dihydroxy benzene disulfonic acid is free from impurities such as small amounts of metal elements. In order to obtain this condition, one has studied a novel method for preparing it, which is part of this invention, from salts of p-dihydroxy benzene monosulfonic acid. To do so, it is necessary to first dehydrate said salt by heating it with liquids forming an azeotrope with water, and by distilling the amount of liquid required to obtain the anhydrous mixture of the salt and solvents. Subsequently, sulfonation is carried out by treating the mixture with the sulfonating acid, so that the sulfate of the salt formed, e.g. potassium sulfate or calcium sulfate, can be separated from the mixture when the reaction is completed.

From the aqueous, alcoholic, or a solution, of the p-dihydroxy benzene disulfonic acid in any other solvent, thus formed and separated from the insoluble salt, the salts of said acid can be obtained either by neutralization or by a salt exchange reaction.

With the appropriate salt, whatever it may be, the following Examples illustrate the preparation of the compounds of this invention.

EXAMPLE 1 bis(methylamine) p-dihydroxy benzene disulfonate a. Preparation of p-dihydroxy benzene disulfonic acid:
190 g of p-dihydroxy benzene monosulfonic acid, 100 ml of dioxane and 100 ml of perchloroethylene are mixed in a flask provided with a reflux condenser. The flask is heated in an oil bath to the reflux temperature (140° C in the oil bath). It is refluxed for half an hour, and then it is left to cool a little to set the condenser for distillation. Two layers are formed in the flask: a colourless lower layer, and a coloured upper layer in which the acid is dissolved. The flask is then heated again, and 100 ml of the mixture of solvents are distilled. In the mixture collected, two layers are formed; the upper one, which is moderate is aqueous. To the flask provided with a reflux condenser, 98 g of sulfuric acid containing 20 % of $SO_3$ are added, and it is heated again, at a lower temperature, so that the reflux is barely noticeable (temperature of the bath: 130° C), for 4 hours, The liquids which accompany the acid are removed by reduced pressure distillation, the residue is dissolved in a little water, 2 g of active charcoal are added, it is filtered. The aqueous solution can be used as such for obtaining the respective salts.

b. Preparation of the methylamine salt:
By adding a methylamine solution to the aqueous solution of the acid prepared as indicated, the methylamine salt is obtained in solution. This solution is treated with active charcoal, filtered, and vacuum-concentrated, so as to obtain a crystalline residue of bis (methylamine) p-dihydroxy benzene disulfonate which, after recrystallizing in water, provides 167 g of pure product, having a melting point of 288° C.

EXAMPLE 2 bis (ethanolamine) p-dihydroxy benzene disulfonate

Neutralization of the acid resulting from the previous operation with 122 g of ethanolamine, followed by filtration and recrystallization, provides 211 g of bis (ethanolamine) p-dihydroxy benzene disulfonate, having a melting point of 182° C.

EXAMPLE 3 bis (phenylamine) p-dihydroxy benzene disulfonate)

a. Preparation of potassium p-dihydroxy benzene disulfonate:
Neutralization of p-dihydroxy benzene disulfonic acid, obtained as indicated in Example 1, with an aqueous solution of potassium hydroxide, gives the potassium salt of said acid. This salt crystallizes and can easily be purified to give an extremely pure product: $C_6H_4O_8K_2S_2$ M.W. = 346, without water of crystallization, which decomposes above 270° C.

b. Preparation of the phenylamine salt:
346 g of the potassium salt, prepared as described above, are dissolved in warm water. Since the solubility of this salt is not high, a liter of distilled water, kept at a temperature of 80°-9° C must be used. On the other hand, in order to prepare the corresponding bitartrate, a solution of 300 g of anhydrous tartaric acid is neutralized with the required amount of aniline, i.e. 186 g of freshly distilled product. The latter solution is poured onto the potassium salt solution, heating and stirring being maintained for 15 minutes. It is left aside to cool, and is left overnight in a refrigerator, the following day the precipitate of potassium bitartrate is filtered off, and the solution is concentrated until it begins to crystallize. After vacuum filtering the solid portion, the product is recrystallized until pure, melting point above 300° C (dec).

EXAMPLE 4 bis (piperazine) p-dihydroxy benzene disulfonate a. Preparation of the potassium salt solution:

As in the preceding Example, 346 g of the potassium salt of p-dihydroxy benzene disulfonic acid are dissolved in 1 liter of distilled water, and the solution is kept warm to prevent crystallization.

b. Preparation of piperazine perchlorate:

To an aqueous solution of perchloric acid, containing 200 g of said acid in 500 ml of water 40 % solution), the amount of aqueous solution of piperazine hexahydrate required for neutralization is added. The required amount of piperazine hexahydrate is 388.46 g ($C_4H_{10}N_2.6H_2O$) dissolved in 500 ml of water. Preferably the pH of the neutralizing solution is controlled to a pH close to 6. The piperazine perchlorate solution is mixed with the warm solution of p-dihydroxy benzene disulfonic acid potassium salt, and is stirred until a copious precipitate of potassium perchlorate is formed, which then increases when the solution is left to cool for several hours. After filtering off the potassium perchlorate, the solution of piperazine p-dihydroxy benzene disulfonate is concentrated in a rotary evaporator, under vacuum, at 60° C, until crystals begin to form, and it is then left in a refrigerator. The product is filtered and recrystallized in water to give 388 g of bis (piperazine) p-dihydroxy benzene disulfonate, having a melting point of 270° C.

EXAMPLE 5 lithium p-dihydroxy benzene disulfonate

2. Preparation of p-dihydroxy benzene disulfonic acid: 190 g of p-dihydroxy benzene monosulfonic acid, 100 ml of dioxane, and 100 ml of perchloroethylene are mixed in a flask provided with a reflux condenser. The flask is heated in an oil bath to the reflux temperature (in the oil bath at 140° ). It is refluxed for half an hour, and then is left to cool a little to set the coolant for distillation. In the flask, two layers are formed: a colourless lower layer, and a coloured upper layer in which the acid is dissolved. The flask is heated again and 100 ml of the solvent mixture are distilled. In the mixture collected, two layers form, the upper, moderate, is aqueous. To the flask provided with a reflux condenser, 98 g of sulfuric acid containing 20 % of $SO_3$ are added, and it is heated again, to a lower temperature, so that the reflux is barely noticeable (bath temperature: 130° C), for 4 hours. The liquids accompanying the acid are removed by distilling at reduced pressure, the residue is dissolved in a little water, 2 g of active charcoal are added, and it is filtered. The solution is concentrated, cooled, and is precipitated by adding five volumes of acetone. The precipitate is filtered, and 189 g of p-dihydroxy benzene disulfonic acid, with a melting point of 166°-169° C are obtained.

b. Preparation of the lithium salt:

270 g of acid obtained according to (a) are dissolved in 2 liters of boiled and oxygen-free distilled water, and the solution is carefully neutralized with 65 g of pure lithium carbonate, the pH being maintained between 6 and 6.5. After filtering the solution is concentrated with the precautions described in paragraph (a), and it is poured into a crystallising dish as soon as the first crystals appear. After cooling, and separating the mother liquors, 300 g of product are obtained which are recrystallized in water. 270 g of lithium p-dihydroxy benzene disulfonate are obtained, having a melting point above 260° C (dec). The infrared spectrum recorded in a KBr pellet gives maxima at the following frequencies: 3480, 3360, 3210, 1690, 1425, 1260, 1205, 1165, 1110, 1035, 885, 825, and 670 cm$^{-1}$.

EXAMPLE 6 calcium p-dihydroxy benzene disulfonate a. Preparation of p-dihydroxy benzene disulfonic acid:

41.6 g diethylamine p-dihydroxy benzene disulfonate (obtained by a known method, but particularly according to Example 1 of Swiss Patent Application No. 7326/72), are dissolved in 500 ml of air-free distilled water. The solution thus obtained is passed through a column of cation exchange resin (Amberlite IRC-50) contaning 60 g of resin prepared in acid form and washed. The liquids are collected in a flask protected from the air (nitrogen atmosphere), and the resin is washed until the eluant no longer gives the reaction of phenols with the ferric chloride solution, then the washings are combined with the main solution. The combined liquids are concentrated in a rotary evaporator, under vacuum, until the solution becomes cloudy, i.e. until the total volume is about 80 ml. When the solution is cold, and before the product crystallizes, 200 ml of pure acetone are added; a crystalline mass is formed which is collected in a Buchner funnel under slight vacuum. After recrystallization in water, 27 g of extremely pure acid are obtained, having a melting point of 166°-169° C.

b. Prepartion of the calcium salt 270 g of the acid obtained according to part (a) are dissolved in 2 liters of boiled, oxygen-free distilled water, and the solution is carefully neutralized with 100 g of pure calcium carbonate, the pH being maintained between 6 and 6.5. The solution is filtered, vacuum concentrated, and left to cool. A crystalline residue of calcium p-dihydroxy benzene disulfonate is obtained which is filtered and washed successively with distilled water, alcohol, and finally with diethyl ether, giving 157 g of pure product having a melting point above 300° C (dec). the infrared spectrum recorded in a KBr pallet gives maxima at the following frequencies: 3500, 1625, 1420, 1340, 1220, 1175, 1110, 1025, 885, and 810 cm$^{-1}$.

EXAMPLE 7 bis (ammonium)-p-dihydroxy benzene disulfonate

The aqueous solution of p-dihydroxy benzene disulfonic acid, obtained according to example 1, is made colorless by filtering after addition of 2 g of charcoal, and then concentrated by evaporation under reduced pressure, until a granular paste is obtained. 100 ml of ether are added, and the thus formed suspension is filtered through a Buchner funnel by suction. The paste obtained is dissolved in 200 ml of distilled water, the solution is filtered and neutralized with concentrated ammonia. After each addition of a portion of ammonia, the pH of the solution is checked, and ammonia addition is stopped at a pH of 6.5. The solution then becomes unclear, and the ammonium salt begins to precipitate.

Without removing the solid particles, the solution is heated to boiling, 1 g of charcoal is added, and the hot solution is filtered through a paper filter. The filtrate is cooled down during several hours, and the precipitated ammonium salt is removed by filtering. After several recristallizations from water, one obtains 92 g of bis (ammonium) p-dihydroxy benzene sulfonate, in the form of a white cristalline powder.

The mother liquids are concentrated, and after recristallization as above described, one obtains 9 g of the same ammonium salt, having a melting point above 320° C. The IR-spectrum measured in KBr gives maxima at 1530, 1410, 1210, 1115, 1020, 890, 820 and 660 cm$^{-1}$.

Other products obtained by the process described:

| | | |
|---|---|---|
| bis (dimethylamine) p-dihydroxy benzene disulfonate | M.P. | 199° C |
| bis (diethylamine) p-dihydroxy benzene disulfonate | M.P. | 198–220° C |
| bis (trimethylamine) p-dihydroxy benzene disulfonate | M.P. | 260° C |
| bis (pyrrolidine) p-dihydroxy benzene disulfonate | M.P. | 272° C |

The compounds of the invention are interesting as hemostatic agents, for their protective action on the capillaries, and as antilipedemic agents.

The pharmacodynamical properties of the products which are the object of this patent are typified by those of bis-diethylamine-p-dihydroxy-benzene-disulfonate.

1. Acute toxicity in the mouse and the rat
   18 to 25 g albino mice
   100 to 150 g Sprague-Dawley rats
   The $LD_{50}$ was determined according to the method of Reed and Muench.

TABLE I

| Administration method | Species | $LD_{50}$ (mg/kg) | Fiducial limits (for p = 0,95) |
|---|---|---|---|
| I.V. | mouse ♂ | 1,016 | (831 – 1,525) |
| I.V. | mouse ♀ | 1,016 | (831 – 1,525) |
| Oral | mouse ♂ | 6,292 | (5,330 – 7,423) |
| Oral | mouse ♀ | 5,878 | (5,286 – 6,532) |
| I.P. | rat ♂ | 2,650 | (2,307 – 3,041) |
| I.P. | rat ♀ | 2,442 | (2,127 – 2,804) |
| Oral | rat ♂ | 5,837 | (4,425 – 7,692) |
| Oral | rat ♀ | 4,678 | (3,978 – 5,493) |

2. Action on the average bleeding time
   bis-diethylamine p-dihydroxy benzene disulfonate produces a decrease of the bleeding time in the rabbit, determined by the method of ROSKAM, modified by LAPORTE (Chemotherapia, 3, 62, 1961). The results obtained one hour after administering the product are given in Table II.

TABLE II

| Dose micromoles / kg | Effect — Percentage decrease of average bleeding time |
|---|---|
| 0.625 | 8.5 % |
| 1.25 | 19.5 % |
| 2.5 | 32.0 % |
| 5.0 | 43.0 % |
| 7.05 | 51.0 % |
| 10.0 | 50.0 % |

3. Activity: time ratio
   The effect of bis-diethylamine p-dihydroxy benzene disulfonate at a dose of 5 micromoles/kg is long lasting, as can be seen from the results given in Table III.

TABLE III

| Time hours after i.v. administration | Effect % decrease of average bleeding time |
|---|---|
| 1 | 43.0 % |
| 2 | 46.8 % |
| 4 | 42.0 % |
| 8 | 33.5 % |
| 16 | 32.0 % |
| 24 | 21.0 % |

4. Protective action on capillaries
   The action of bis diethylamine p-dihydroxy benzene disulfonate on the capillary permeability for the mouse was determined by the modified method of BEACH-STEINITZ (J. Pharmacol. Exp. Ther. 131 (1), 400, 1961). The product, administered i.p., causes a decrease of the capillary permeability which appears after 8 micromoles/kg, and higher doses, and the maximum effect is attained at a dose of 200 micromoles/kg. Intermediate doses produce effects proportional to the logarithm of the dose.

5. Hypolipedemic action in the rat
   Bis-diethylamine-p-dihydroxy-benzene disulfonate significantly inhibits the increase of the plasma cholesterol, triglyceride, and total lipids levels in Sprague-Dawley rats treated with Triton WR-1339 (Friedmann M. and Byers S.O., J. Exptl. Med., 97, 117, 1953). The results obtained are given in Table IV.

TABLE IV

| | TRITON | TRITON + BIS DIETHYLAMINE P-DIHYDROXY BENZENE DISULFONATE |
|---|---|---|
| TOTAL CHOLESTEROL mg % (plasma) | 238.4 ± 6.5 | 223.0 ± 15.1 |
| Δ % with respect to Triton | | − 6 % |
| P | | 0.15<P<0.20 |
| FREE CHOLESTEROL mg % (plasma) | 60.5 ± 2.5 | 54.4 ± 3.9 |
| Δ % with respect to Triton | | − 10 % |
| P | | 0.05<P<0.10 |
| TRIGLYCERIDES mg % (plasma) | 773.5 ± 59.1 | 589.5 ± 57.9 |
| Δ % with respect to Triton | | − 24 % |
| P | | 0.0125<P<0.025 |
| TOTAL LIPIDS mg % (plasma) | 2466.9 ± 141.2 | 2001.9 ± 193.7 |
| Δ % with respect to Triton | | − 19 % |
| P | | 0.025<P<0.05 |

The following table gives the values for $DL_{50}$ and $DE_{50}$, as well as proposed doses of some compounds according to the present invention.

|  | DL$_{50}$ (mg/kg) | DE$_{50}$ (μmoles/kg) | Proposed dose in g/day | | |
|---|---|---|---|---|---|
|  |  |  | Rectal | Oral | Parenteral |
| bis (piperazine) p-dihydroxy-benzene disulfonate | >2000 (p.o.) | 1,25 | 1 – 2 | 1 – 2 | 0,25 – 1 |
| lithium p-dihydroxybenzene-disulfonate | 2186 (i.v.) | 0,90 | 1 –0 2 | 1 – 2 | 0,25 – 1 |
| calcium p-dihydroxybenzene-disulfonate | >6880 (p.o.) | 0,98 | 1 – 2 | 1 – 2 | 0,25 – 1 |
| bis (diethylamine) p-dihydroxy-benzene disulfonate | 1016 (i.v.) | 2,25 | 1 – 2 | 1 – 2 | 0,25 – 1 |
| bis (ammonium) p-dihydroxy-benzene disulfonate | 1209 | 2,45 | 1 – 2 | 1 – 2 | 0,25 – 1 |

| Example of formulation per tablet (500 mg dose) | |
|---|---|
| bis diethylamine p-dihydoxy benzene disulfonate | 0.500 g |
| Rice starch | 0.100 g |
| Lactose | 0.100 g |
| Polyvinylpyrrolidone | 0.020 g |
| Magnesium stearate | 0.003 g |
| Weight of tablet | 0.723 g |

| Example of formulation per capsule (250 mg dose) | |
|---|---|
| bis diethylamine p-dihydroxy benzene disulfonate | 0.250 g |
| Lactose | 0.050 g |
| Aerosil | 0.001 g |
| Magnesium stearate | 0.002 g |
| Weight of capsule | 0.303 g |

| Example of formulation for suppositories (500 mg dose) | |
|---|---|
| bis diethylamine p-dihydroxy benzene disulfonate | 0.500 g |
| Citric acid | 0.0036 g |
| Sodium metabisulfite | 0.0002 g |
| Monolene | 1.650 g |
| Weight of suppository | 2.15 g |

| Example of formulation per injectable phial (250 mg dose) | |
|---|---|
| bis diethylamine p-dihydroxy benzene disulfonate | 0.250 g |
| Sodium metabisulfite | 0.002 g |
| Twice distilled water | 2 ml |

For the other products of the series, the doses are within the values given above.

I claim:

1. A medicament having hemostatic action, a protective action on capillaries, and antilipemic qualities comprising a pharmaceutically acceptable carrier and a phramaceutically effective amount of bis (piperazine) p-dihydroxybenzene disulfonate.

2. A medicament having hemostatic action, a protective action on capillaries, and antilipemic qualities comprising a pharmaceutically acceptable carrier and a pharmaceutcially effective amount of lithium p-hydroxybenzene disulfonate.

3. A medicament having hemostatic action, a protective action on capillaries, and antilipemic qualities comprising a pharmaceutically acceptable carrier and a pharmaceutically effective amount of calcium p-dihydroxybenzene disulfonate.

4. A medicament having hemostatic action, a protective action on capillaries, and antilipemic qualities comprising a pharmaceutically acceptable carrier and a phramaceutically effective amount of bis (diethylamine) p-dihydroxybenzene disulfonate.

5. A medicament having hemostatic action, a protective action on capillaries, and antilipemic qualities comprising a pharmaceutically accepable carrier and a pharmaceutcially effective amount of bis (ammonium) p-dihydroxybenzene disulfonate.

6. A method of combating hemorrhages and fragility of the capillaries comprising administering a composition of bis (piperazine) p-dihydroxybenzene disulfonate at the dose of 1 to 2 g per day orally or rectally, or administering parenterally at the dose of 250 to 1,000 mg per day.

7. A method of combating hemorrhages and fragility of the capillaries comprising administering a composition of lithium p-dihydroxybenzene disulfonate at the dose of 1 to 2 g per day orally or rectally, or administering parenterally at the dose of 250 to 1,000 mg per day.

8. A method of combating hemorrhages and fragility of the capillaries comprising administering a composition of calcium p-dihydroxybenzene disulfonate at the dose of 1 to 2 g per day orally or rectally, or administering parenterally at the dose of 250 to 1,000 mg per day.

9. A method of combating hemorrhages and fragility of the capillaries comrising administering a composition of bis (diethylamine) p-dihydroxybenzene disulfonate at the dose of 1 to 2 g per day orally or rectally or administering parenterally at the dose of 250 to 1,000 mg per day.

10. A method of combating hemorrhages and fragility of the capillaries comprising administering a composition of bis (ammonium) p-dihydroxybenzene disulfonate at the dose of 1 to 2 g per day orally or rectally, or administering parenterally at the dose of 250 to 1,000 mg per day.

11. A medicament having hemostatic action, a protective action on capillaries, and antilipemic qualities, comprising a pharmaceutically acceptable carrier and a pharmaceutically effective amount of bis (methylamine) p-dihydroxy benzene disulfonate.

12. A medicament having hemostatic action, a protective action on capillaries, and antilipemic qualities, comprising a pharmaceutically acceptable carrier and a pharmaceutically effective amount of bis (ethanolamine) p-dihydroxy benzene disulfonate.

13. A medicament having hemostatic action, a protective action on capillaries, and antilipemic qualities, comprising a pharmaceutically acceptable carrier and a pharmaceutically effective amount of bis (phenylamine) p-dihydroxy benzene disulfonate.

14. A medicament having hemostatic action, a protective action on capillaries, and antilipemic qualities, comprising a pharmaceutically acceptable carrier and a pharmaceutically effective amount of bis (piperazine) p-dihydroxy benzene disulfonate.

15. A medicament having hemostatic action, a protective action on capillaries, and antilipemic qualities, comprising a pharmaceutically acceptable carrier and a pharmaceutically effective amount of bis (dimethylamine) p-dihydroxy benzene disulfonate.

16. A medicament having hemostatic action, a protective action on capillaries, and antilipemic qualities, comprising a pharmaceutically acceptable carrier and a pharmaceutically effective amount of bis (trimethylamine) p-dihydroxy benzene disulfonate.

17. A medicament having hemostatic action, a protective action on capillaries, and antilipemic qualities, comprising a pharmaceutically acceptable carrier and a pharmaceutically effective amount of bis (pyrrolidine) p-dihydroxy benzene disulfonate.

18. A method of combating hemorrhages and fragility of the capillaries comprising administering a composition of bis (methylamine) p-dihydroxy benzene disulfonate at the dose of 1 to 2 g per day orally or rectally, or administering parenterally at the dose of 250 to 1,000 mg per day.

19. A method of combating hemorrhages and fragility of the capillaries comprising administering a composition of bis (ethanolamine) p-dihydroxy benzene disulfonate at the dose of 1 to 2 g per day orally or rectally, or administering parenterally at the dose of 250 to 1,000 mg per day.

20. A method of combating hemorrhages and fragility of the capillaries comprising administering a composition of bis (phenylamine) p-dihydroxy benzene disulfonate at the dose of 1 to 2 g per day orally or rectally, or administering parenterally the dose of 250 to 1,000 mg per day.

21. A method of combating hemorrhages and fragility of the capillaries comrising administering a composition of bis (dimthylamine) p-dihydroxy benzene disulfonate at the dose of 1 to 2 g per day orally or rectally, or administering parenterally the dose of 250 to 1,000 mg. per day.

22. A method of combating hemorrhages and fragility of the capillaries comprising administering a composition of bis (trimethylamine) p-dihydroxy benzene disulfonate at the dose of 1 to 2 g per day orally or rectally, or administering parenterally the dose of 250 to 1,000 mg per day.

23. A method of combating hemorrhages and fragility of the capillaries comprising administering a composition of bis (pyrrolidine) p-dihydroxy benzene disulfonate at the dose of 1 to 2 g per day orally or rectally, or administering parenterally the dose of 250 to 1,000 mg per day.

* * * * *